United States Patent
Hirsch et al.

(10) Patent No.: US 9,962,300 B1
(45) Date of Patent: May 8, 2018

(54) SENSOR AND HOUSING

(71) Applicants: Gary F Hirsch, Redwood City, CA (US); Frederic Lam, Hong Kong (CN)

(72) Inventors: Gary F Hirsch, Redwood City, CA (US); Frederic Lam, Hong Kong (CN)

(*) Notice: Subject to any disclaimer, the term of this patent is extended or adjusted under 35 U.S.C. 154(b) by 0 days. days.

(21) Appl. No.: 15/230,411

(22) Filed: Aug. 6, 2016

Related U.S. Application Data (60) Provisional application No. 62/202,239, filed on Aug. 7, 2015.

(51) Int. Cl.
```
G08B 21/00      (2006.01)
A61F 13/42      (2006.01)
G01D 11/24      (2006.01)
G01N 27/22      (2006.01)
G08B 21/20      (2006.01)
```

(52) U.S. Cl.
CPC ............ *A61F 13/42* (2013.01); *G01D 11/245* (2013.01); *G01N 27/223* (2013.01); *G08B 21/20* (2013.01); *A61F 2013/424* (2013.01)

(58) Field of Classification Search
CPC ...... A61F 13/42; G08B 21/20; G01N 27/223; G01D 11/245
USPC ....................................................... 340/604
See application file for complete search history.

(56) References Cited

U.S. PATENT DOCUMENTS

| | | | |
|---|---|---|---|
| 5,760,694 A | 6/1998 | Nissim et al. | |
| 5,903,222 A | 5/1999 | Kawarizadeh et al. | |
| 5,908,411 A | 6/1999 | Matsunari | |
| 6,097,297 A * | 8/2000 | Fard | A61F 13/42 340/604 |
| 6,832,507 B1 | 12/2004 | de Berg et al. | |
| 6,916,968 B2 * | 7/2005 | Shapira | A61F 13/42 340/604 |
| 7,250,547 B1 * | 7/2007 | Hofmeister | A61F 13/42 340/604 |
| 7,605,710 B2 * | 10/2009 | Crnkovich | A61F 13/42 340/604 |
| 7,952,366 B2 | 5/2011 | Philipp et al. | |
| 7,973,667 B2 * | 7/2011 | Crnkovich | A61F 13/42 340/604 |
| 8,395,014 B2 | 3/2013 | Helmer et al. | |

(Continued)

FOREIGN PATENT DOCUMENTS

EP          0446821 A2    3/1991

OTHER PUBLICATIONS

Atmel AT42QT1010 datasheet, retrieved May 26, 2015, Atmel Corp.1600 Technology Drive San Jose, CA 95110 http://www.atmel.com/images/atmel-9541-at42-qtouch-bsw-at42qt1010_datasheet.pdf, posted May 22, 2013.

(Continued)

*Primary Examiner* — John A Tweel, Jr.
(74) *Attorney, Agent, or Firm* — Edward S. Sherman (57) ABSTRACT

An elongated hand held sensor is removable from a strap for use. The strap can also be used to form a loop that is attached to another object, such as a handle or other fixture, such as a bedroom furnishing. The sensor may contain an electrode at one end in signal communication with a capacitive measurement circuit on a circuit board in the sensor device housing. The electrode is optionally shaped to have adjacent portions that match the non-planar shape at the distal end of the housing.

16 Claims, 13 Drawing Sheets

(56) References Cited

U.S. PATENT DOCUMENTS

| | | |
|---|---|---|
| 8,421,636 B2 * | 4/2013 | Collette .................. A61F 13/42 340/604 |
| 8,725,245 B2 | 5/2014 | Feldkamp et al. |
| 8,797,049 B2 | 8/2014 | Pedersen et al. |
| 8,866,624 B2 | 10/2014 | Ales, III et al. |

OTHER PUBLICATIONS

URL to Kickstarter campaign: https://www.kickstarter.com/projects/1587823871/wet-diaper-detector-keychain-children-and-nursing/comments accesses Oct. 25, 2015. Landing page co-submitted as PDF file.

URL to website selling product::https://thediapercheck.com/instructions.php, accessed Oct. 25, 2017. Landing page co-submitted as PDF file.

\* cited by examiner

*PRIOR ART*

SENSOR AND HOUSING

CROSS REFERENCE TO RELATED APPLICATIONS

The present application claims the benefit of priority to the US Provisional patent application that was filed on Aug. 7, 2016, having application No. 62/202,239, and is incorporated herein by reference.

BACKGROUND OF INVENTION

The field of inventions is hand held sensor devices, as well as hand held sensors for detecting moisture, and more particularly moisture sensors for the external detection of urine in diapers.

Hand held sensors are easily damaged, lost or misplaced between uses.

There is a need for an improved hand held sensor that is both durable, and can be placed or attached in a workspace, as well as easily transported without being difficult to access.

The is also a need for moisture sensors for the external detection of urine in diapers that have an appropriate sensitivity to provide the user with practical information that minimize false negative and positive readings for variables unrelated to the need to change of diaper.

The above and other objects, effects, features, and advantages of the present invention will become more apparent from the following description of the embodiments thereof taken in conjunction with the accompanying drawings

SUMMARY OF INVENTION

In the present invention, the first object is achieved by providing a device for sensing comprising an elongated housing with a sensing end and an opposing distal end adapted to receive a strap, a flexible elongated strap attached to the distal end of said housing at a proximal end thereof, the strap having at the opposing distal end a closed loop adapted to receive the elongated housing which can be passed entirely through the closed loop to form a secondary connection loop around another article.

Other objects of the invention are achieved by one or more of the second and following aspects in which a second aspect of the invention is characterized by device for sensing comprising a portable housing, a capacitive sensing circuit disposed in the housing and having a sensing electrode disposed at a distal end of the housing, a source of power for energizing the circuit, a means for communicating when the capacitive sensing circuit has detected a predetermined quantity of urine absorbed in a diaper material.

Another aspect of the invention is characterized by a device for sensing comprising a portable housing a capacitive sensing circuit disposed in the housing and having a sensing electrode disposed at a distal end of the housing, a source of illumination of the field of use of the sensing device that is at least one of directed towards or emanating from the distal ends of the housing, a source of power for energizing the circuit, at least one externally visible indicator light that is energized by the power source when the electrode has detected a predetermined quantity of urine absorbed in a diaper material.

Another aspect of the invention is characterized by any such device for sensing further comprising a capacitive sensing circuit having an externally switchable capacitor to adjust the sensitivity of the device.

Another aspect of the invention is characterized by any such device for sensing wherein the capacitive sensing circuit is a digital burst mode charge transfer sensor.

Another aspect of the invention is characterized by any such device for sensing wherein the capacitive sensing circuit deploys an electrode with connected planar portions that are not in parallel planes to each other.

Another aspect of the invention is characterized by any such device for sensing wherein the capacitive sensing circuit deploys an electrode with a pin shape terminating in a head that is disposed outside the elongated housing.

Another aspect of the invention is characterized by any such device for sensing wherein the capacitive sensing circuit deploys an electrode with a pin shape terminating in a head that is disposed outside the elongated housing.

Another aspect of the invention is characterized by any such device for sensing wherein the capacitive sensing circuit is a digital burst mode charge transfer sensor with a resistive component in series connection to the sensing electrode a first capacitor component connecting said resistive component to the digital burst mode charge transfer sensor, a second capacitive component connected to ground in a parallel circuit between said resistive component and said first capacitor.

The above and other objects, effects, features, and advantages of the present invention will become more apparent from the following description of the embodiments thereof taken in conjunction with the accompanying drawings.

BRIEF DESCRIPTION OF DRAWINGS

FIG. 1A is a top plan view of the sensor and housing, whereas

FIG. 6A-C is a schematic circuit diagram of another embodiment of the sensing circuit, which includes the power supply (FIG. 6C) and battery power indicator (FIG. 6B)

FIG. 8A a top plan view of a preferred embodiment of the electrode for the circuit of FIG. 5 or 6A, whereas

FIG. 9A is a side elevation view of an alternative embodiment of the sensor and housing that includes a light source, whereas

DETAILED DESCRIPTION

Referring to FIGS. 1A through 13B, wherein like reference numerals refer to like components in the various views, there is illustrated therein a new and improved sensor and housing, generally denominated 100 herein.

In accordance with the present invention the sensor and housing 100 comprises an elongated sensor housing 110 with a sensing end 111 and an opposing distal end 112 adapted to receive an elongated strap 120. The elongated strap 120 is flexible and attached to the distal end 112 of said sensor at a proximal end 121 thereof. The strap 120 has at the opposing distal end 122 a closed loop 123 adapted to receive the elongated sensor housing 110, which can be passed entirely through the inner perimeter 124 of the closed loop 123 to form a secondary connection loop around another article. Strap 120 is preferably at least twice the length of the sensor housing 110 in the axial or major axis thereof. Strap 120 has a detent style connector coupling 125 adopted to be received in the distal end of the elongated sensor housing 110, or the extension cord 121 attachable thereto via passage 126. The sensor housing 110 or attachable cord has a complimentary receiving coupling 125.

The strap 120 is attached to another articles, such as a tool, or diaper bag 10 handle 11, by forming a secondary loop when the flexible handle straddles a bag handle after the sensor 110 is inserted into the perimeter 124, and then moved away to close the secondary loop 134 formed therein on the handle.

Another and more preferred embodiment of the invention is that the sensor 100 comprises a capacitive test circuit 1000 that is energized by a power supply, which is preferably a battery 1010. In a most preferred embodiment the circuit 1000 is configured for detecting moisture in a distal object. To wit, the detection of urine in diaper without the need to open and inspect the diaper, and to do so without removing clothing from the wearer. In such embodiments, the sensor housing 110 has external controls and external indicators to respectively energize the capacitive circuit 1000 and indicate circuit detection status to the user.

Figure 1A:
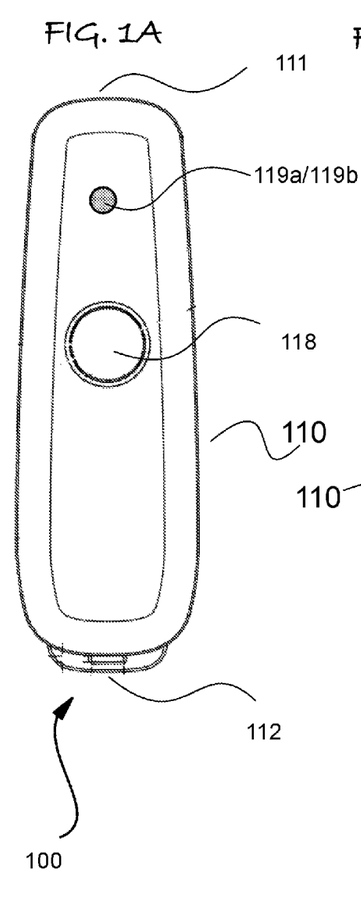
Figures 1B, 1C:
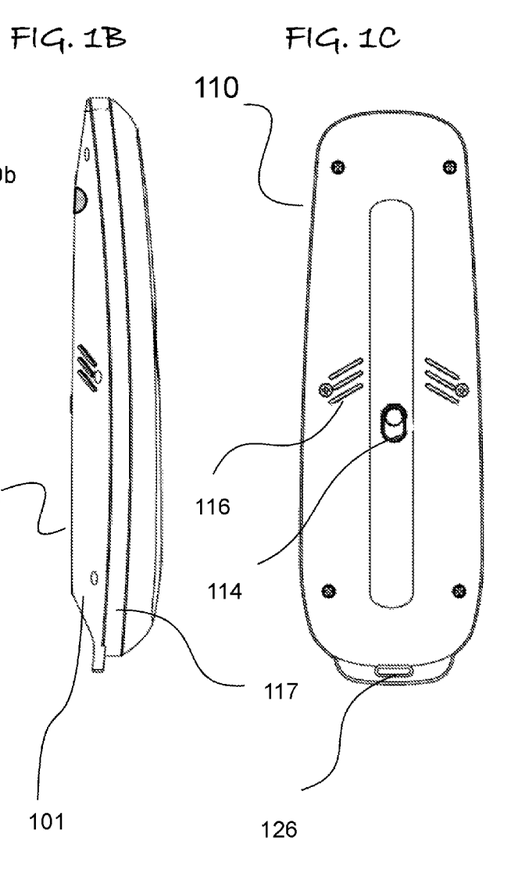
FIG. 1B is a side elevation view and FIG. 1C is a bottom plan view thereof.
Figures 2A, 2B:
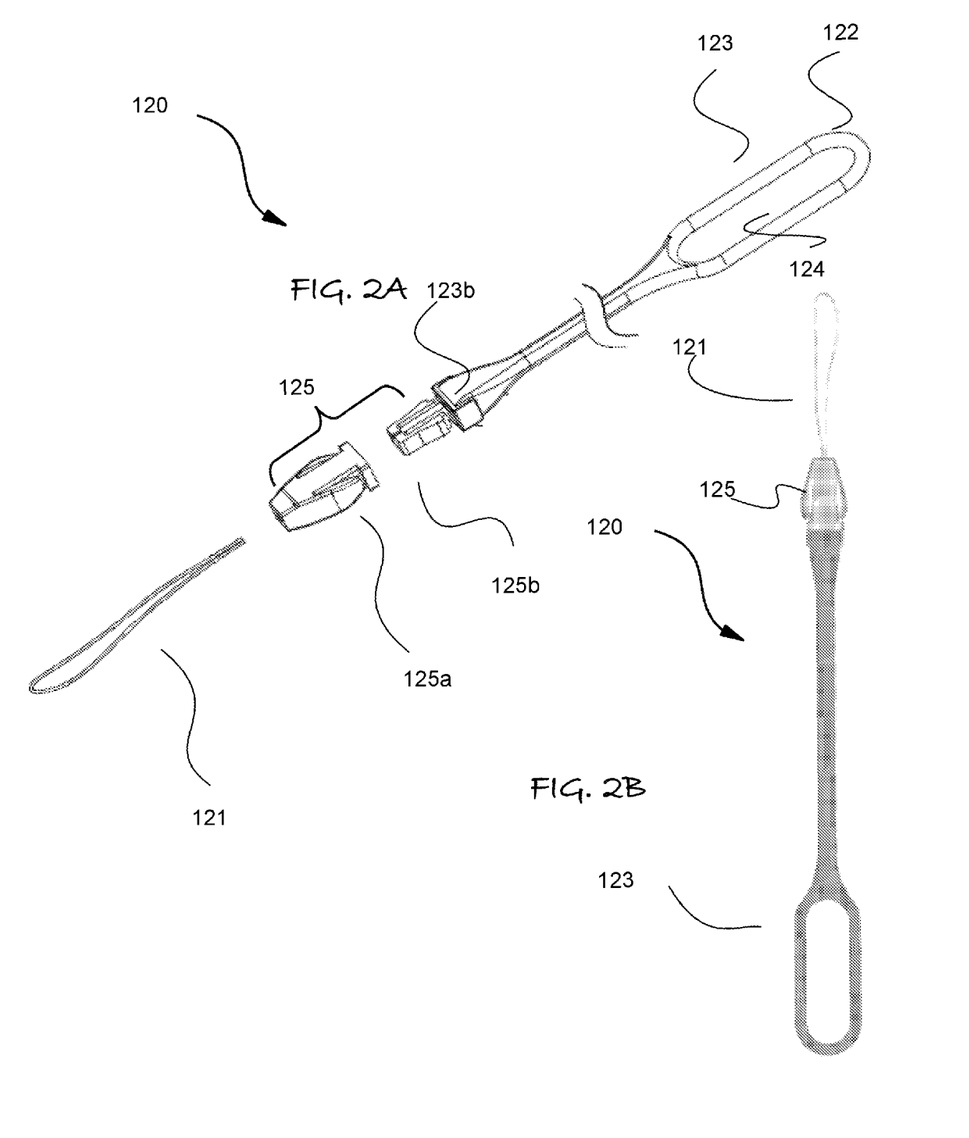
FIG. 2A is an exploded perspective view of the strap and FIG. 2B is a top plan view of the assembled strap.
Figure 3:
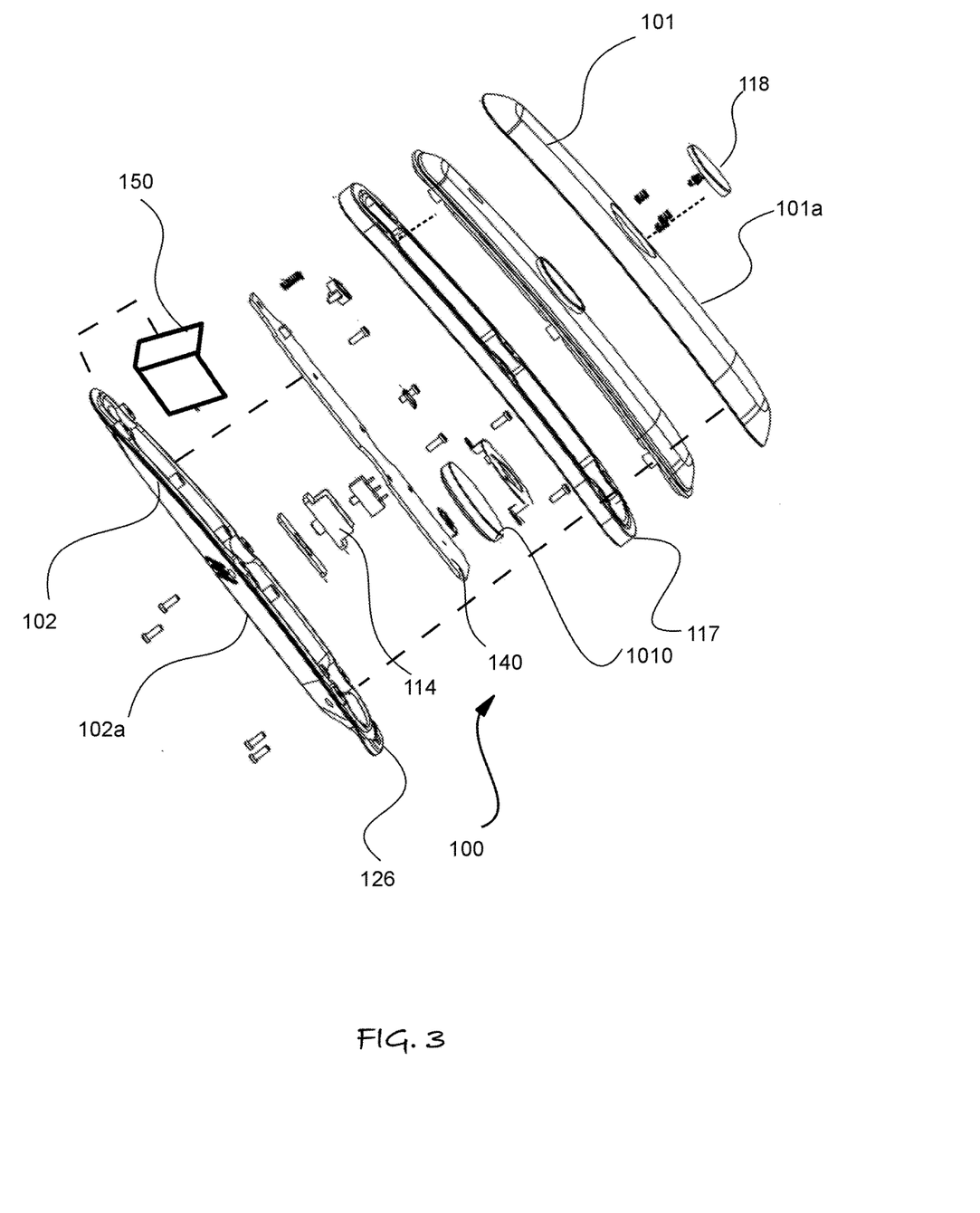
FIG. 3 is an exploded perspective view of the sensor and housing.

The sensor portion is preferably an electronic circuit 1000 on a printed circuit board 140 disposed with the housing 110, as shown in the exploded view in FIG. 3.

The elongated sensor housing 110 is also preferably constructed of an upper 101 and lower shell 102, each having respective exterior surfaces 101a and 102a that are on a concave portion to define an internal cavity for housing the sensor circuit 1000 partly on PC board 140 with the connected electrode 150 disposed at the end 111 opposite the strap 120 connection end 112.

The sensor housing 110 also preferably has a series of ridges 116 on at least one of two-opposing upper and lower surfaces, but more preferably surface 102a. The sensor housing 110 also preferably has a peripheral bumper 117 disposed between the upper and lower surfaces that is pliable to absorb energy and protect the more rigid case or housing portions 100 if dropped. The sensor 100 optionally has at least one activation switch 118 on an upper or lower surface of the housing 110. The sensor 100 also preferably has an illumination light source 130 (FIGS. 9, 10B, 11D and 12) disposed opposite or pointed toward or to illuminate the sensing end 111 of the housing 110, or projecting light from the sensing end of the housing 110. The sensor 100 preferably includes one or more indicator lights 119a and/or 119b. More preferably, the indicator lights 119a and 119b are on the same side of the sensor housing 110 as the activation switch 118. The indicator light 119a and 119b can appear to the user to be in the same location in the housing 110, but be separate LED lights of different color s to indicate the sensor circuit is energized by the battery 1010 when the switch 118 is depressed, and the that water is detected when the other light of a different color is energized by the sensing circuit.

Another aspect of the invention is that the sensor 100 also preferably deploys a capacitive circuit 1000 within sensor housing 110 to detect external moisture, such as urine in a diaper or other absorbent member. The sensor housing 110 is also preferably water proof, having seals or sealing gaskets at each potential opening or moving part, in which case a flexible bumper 117 can be configured to provide a sealed gasket between the upper 101 and lower 102 shells of the housing 110, shown in the exploded view of FIG. 3.

While the desirability to use a handheld capacitive sensor device externally for diaper testing has been suggested, it has been discovered by the inventors that it is very difficult to obtain a sufficiently repeatable signal for use with a broad range of commercial diapers, as well as to account for the presence of clothing and variability of placement by the user.

A general issue with measuring moisture in diapers by a capacitive sensor is that urine will spread and disperse as it is absorbed, which in part also depends on the current saturation state of the absorbent material, which is generally not monolithic. Hence, the success of a particular sensor configuration to operate under such a broad range of conditions is not predictable.

The inventors have also discovered that in general a sensor must not be so sensitive that the results vary with external placement of the device, as well as proximity of the electrode to the potential location of moisture. To this end it would be desirable to construct a device that is sensitive from a farther distance, beyond the potentially swollen absorbent material in the diaper and diaper skin, as well as clothing, to avoid the output variation from the spread and dispersal of urine. However, as distance is increased the signal to noise ratio decreases.

A sufficient output for sensing at least about 50 ml of absorbed urine at distances greater than about 0.5 to about 5 mm has been achieved by the choice of electrode size, shape and circuit type, as well as circuit parameters, as disclosed in the various electrical schematics and parameters of FIGS. 4-7, 13A and 13B.

The sensor capacitive circuit 1000 is preferably a digital burst mode charge transfer mode sensor such as the Atmel QT® IC devices, available from Atmel Corp. and generally described in the following patents, which are incorporated herein by reference: U.S. Pat. No. 7,952,366 (Philip et al.) issued May 31, 2011 and U.S. Pat. No. 8,797,049(Pedersen et al.) issued Aug. 5, 2014. Other forms of capacitive sensing devices for sensing moisture include the disclosure of U.S. Pat. No. 8,866,624 (Ales et al.), which is also incorporated herein by reference.

Figure 4A:
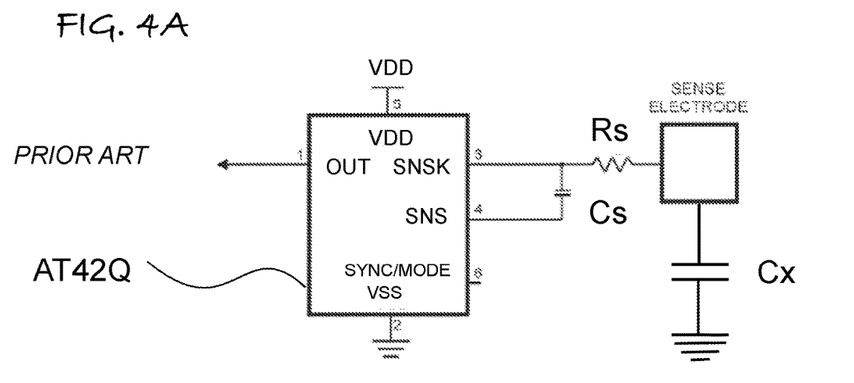
FIG. 4A and FIG. 4B are schematic circuit diagrams of the prior art and improved sensor circuitry respectively.
Figure 4B:
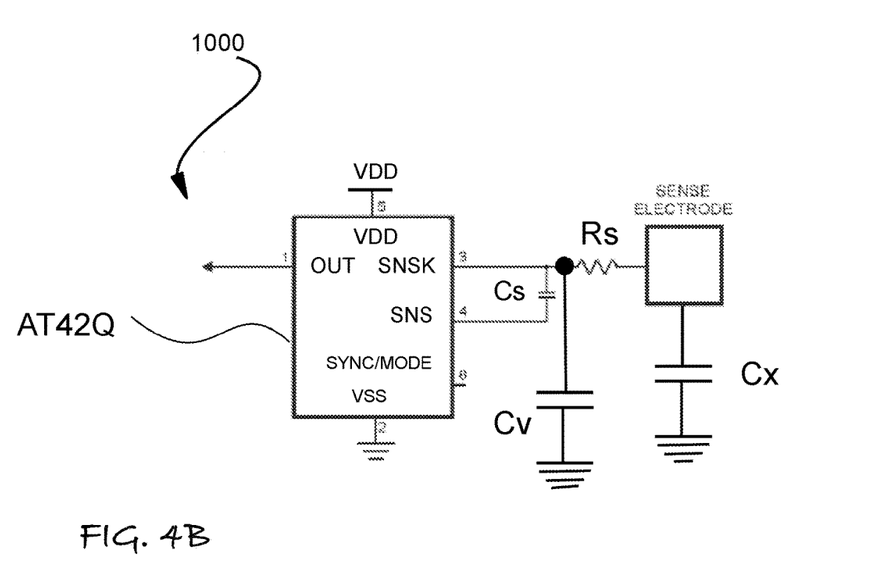

FIG. 4A discloses such a prior art Atmel chip in a generic capacitive sensing circuit with electrode 150, with Cx representing the load capacitance. One aspect of the invention is the use of the Atmel chip (or a general type burst mode charge transfer sensor) as shown in FIG. 4B, is a modification thereto that in part enables the noted improvements for sensing moisture in diapers. Compared with the recommended circuit topography of the Atmel chips shown in FIG. 4A for touch screen application, the inventive embodiments of FIG. 4B inserts another or second capacitor in a capacitive connection to ground (Cv) between the connection of the Cs and Rs components. The Rs (resistive component) is inserted between the electrode 150 and the point of a parallel connection of a first capacitor (Cs) to the first pin (SNS 4) of the circuit in the AT42Q IC and the other parallel path the second pin (SNSK 3).

Figure 5:
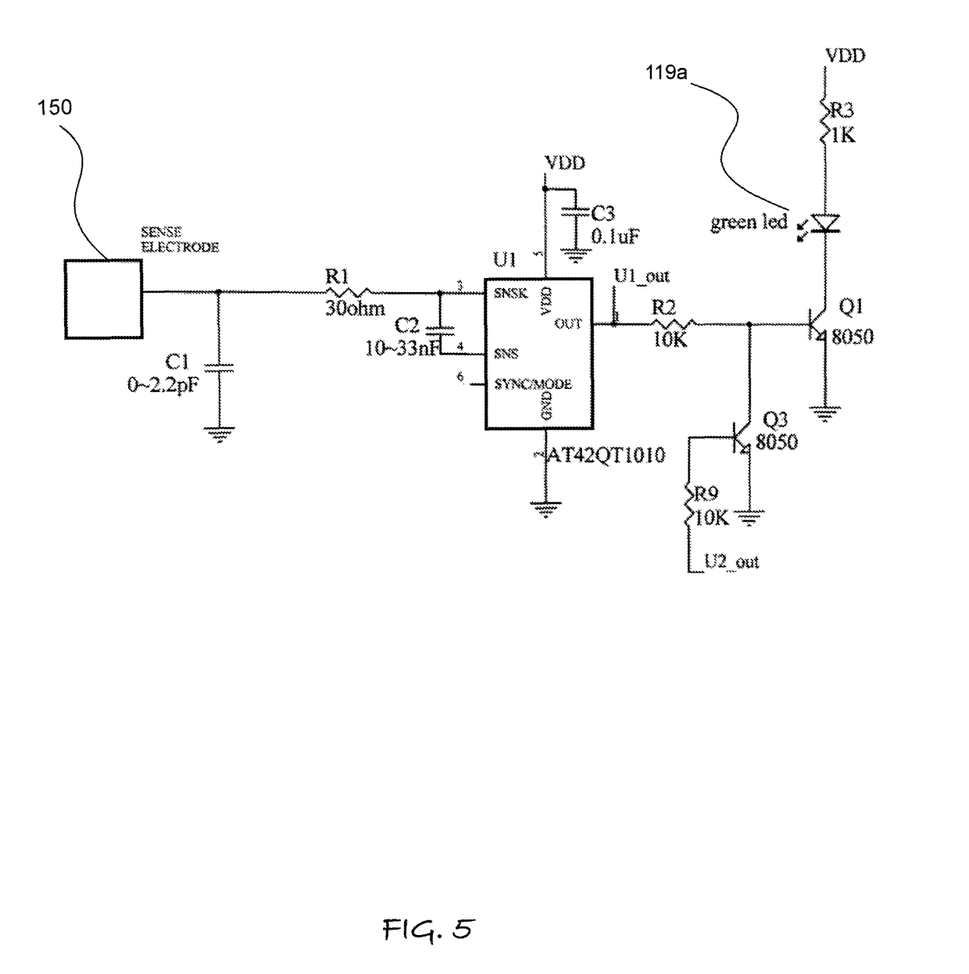
FIG. 5 is a schematic circuit diagram of a portion of the sensing circuit in an embodiment of the invention.

The circuit in FIG. 5, with the indicated range of R and C values, can generally provide detection of 30-50 ml or urine at distances of 0-2 mm to indicate that the diaper or pad should be manually checked, or has absorbed some urine. Even the indication of some urine is useful when the diaper still has further absorptive capacity, as this indicates is should be checked more frequently either with the device 100 or manually to replace it promptly.

Figure 6A:
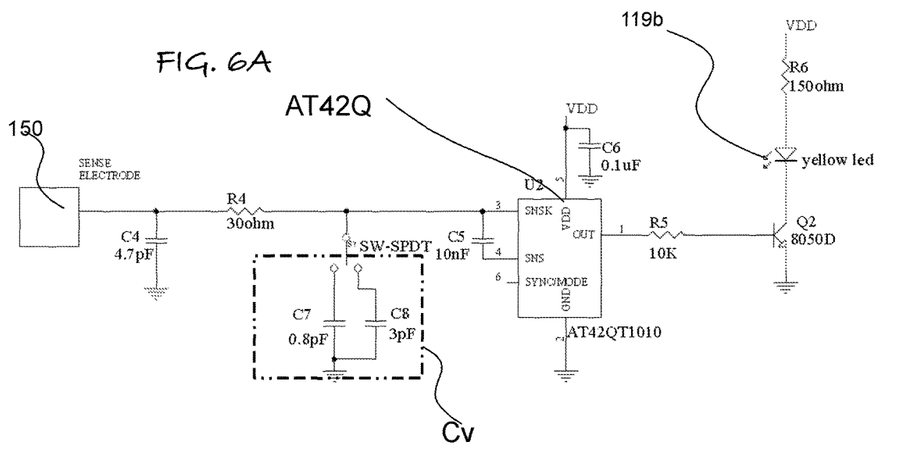
Figure 6B:
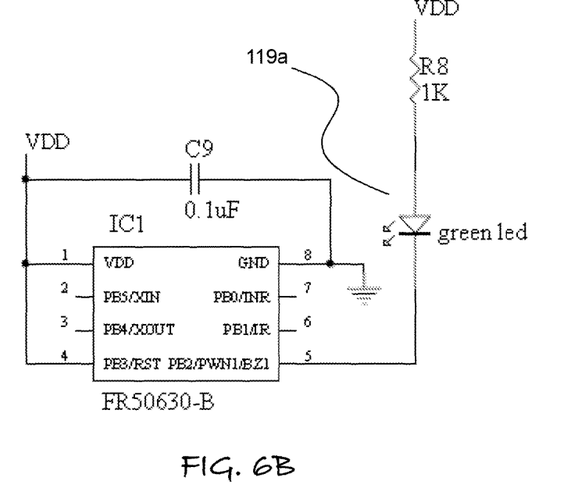
Figure 6C:
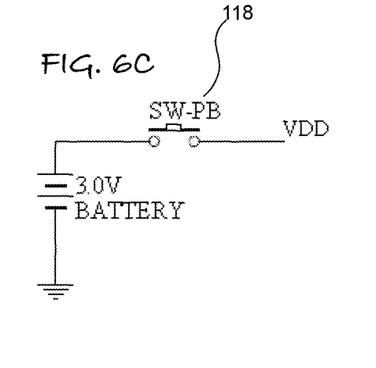

In the more preferred circuit of FIG. 6A-C, the IC1 device in (FIG. 6B) energizes the green LED 119b when the main power switch 118 is activated and the battery 1010 has sufficient power to energize the Atmel chip (AT4QT1010) indicated by the lead line labeled AT42Q. Thereafter, in use when the electrode end 111 of the sensor 100 is placed proximal to a suspected wet diaper, the IC1 device (FIG. 6B) is energized and if the measured change in circuit response is sufficient, then the signal sent at pin 1 (OUT) is sufficient to energize and light the yellow LED (119a), and optionally turn off the green LED, such as via another integrated circuit (IC). The transistors Q2 or Q1 and Q3 switch on to energize the yellow LED upon receipt of the digital output of pin 1 (OUT).

Figure 7:
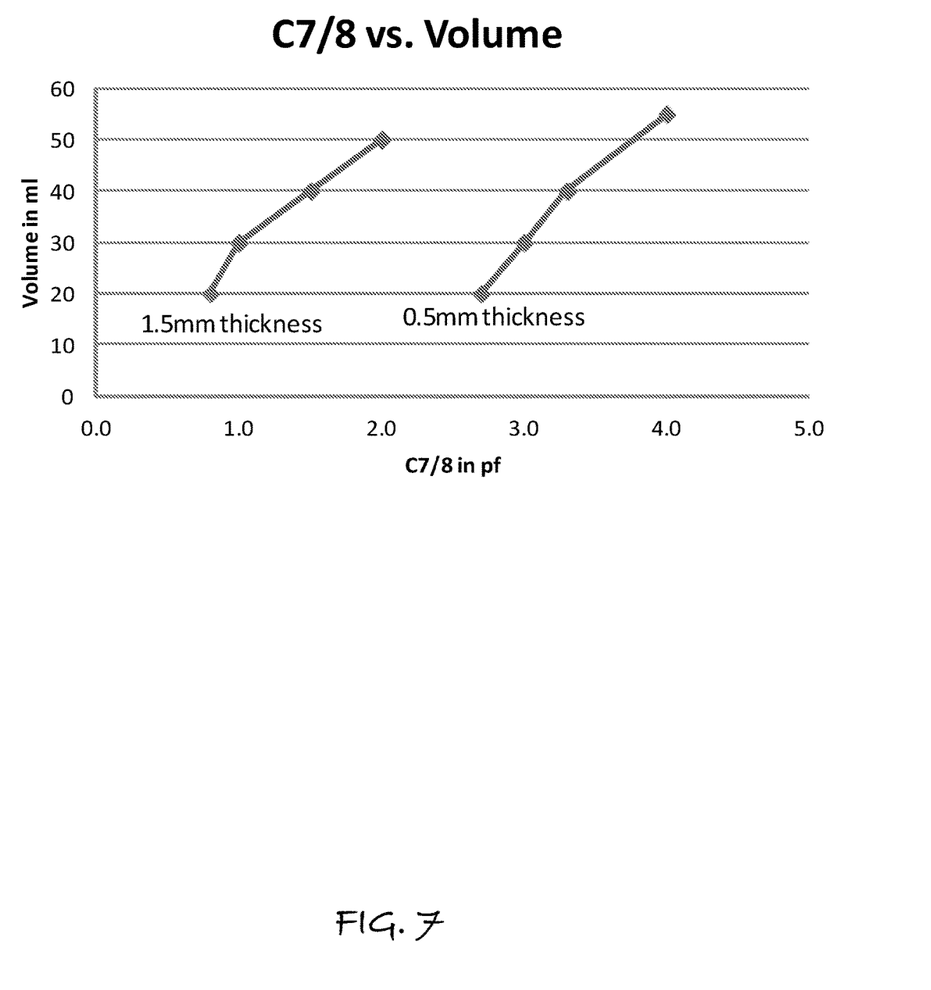
FIG. 7 is a graph of the optimum Cv values for triggering the OUT pin in FIG. 7A to detect different urine volumes at either 0.5 or 1.5 mm distance from the diaper.
Figure 8A:
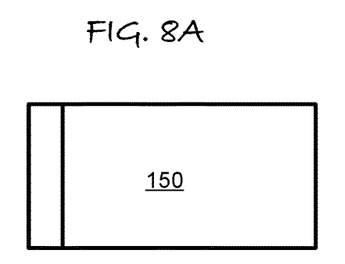
Figure 8B:
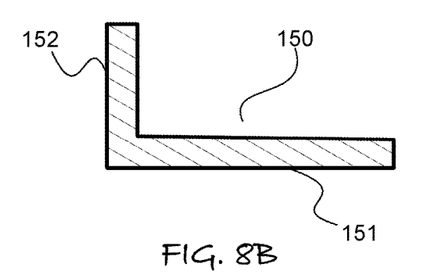
FIG. 8B is a sectional elevation view thereof.
Figure 8C:
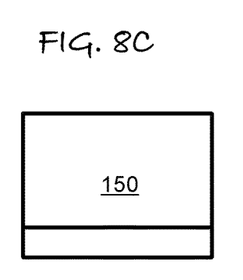
FIG. 8C is a front elevation view thereof and FIG. 8D is a back elevation view thereof.
Figure 8D:
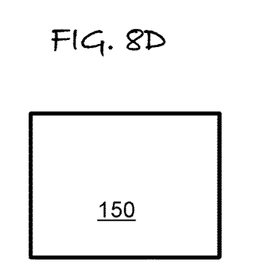

In this more preferred embodiment of FIG. 6A, the value of Cv is switchable (via switch 114) to select alternative Cv capacitors C7 or C8. Further, the values of capacitors C4, C5, R4 provide a sufficient sensitivity such that the selection of either C7 or C8 as Cv with the switch SW-SPDT 114 allows a moisture detection threshold of 30 ml at the distance of 0.5 to 1.5 mm (by selecting C7 or C8) to account for variations in clothing thickness. Electrode 150 is copper or brass and measures about 18 by 12.6 mm. FIG. 7 plots the optional volume sense threshold at the distance of 0.5 and 1.5 mm as a function of Cv. Hence, the value of Cv selected via switch 114 allows a distance range to be selected for sensing the moisture quantity desired. The distance from the clothing and/or diaper will vary when it is covered by clothing. The moisture detection threshold can be shifted upwards of 30 ml as well.

In an analog circuit equivalent of the Atmel AT42Q chip, the R4, C5, C7 and C8 values would be selected to give a sufficiently high output voltage of the equivalent circuit so that the output value would correspond with the quantity of urine in the diaper, typically between about 20 to 60 ml in a spot or spread within the absorbent material in a diaper. The change in output voltage should be large enough with respect to absorbed urine volume that the device will work over a repeatable distance range that takes into account external clothing and variances among users in holding the device. The change in output voltage signal with respect to urine volume should be several times greater than with respect to potential distance variations. This could be similarly be accomplished by a sensitivity switch 114 on the bottom of the device 100, which selects either C7 or C8, or an alternative component, or any combination of values of C4, R4, C5 and Cv.

It should be appreciated that the alternative values of C7 and C8 are likely to be different, as shown in FIG. 7 when it is desirable to sense a greater amount of urine, from alternative distance or distance ranges, and may require further variation in C4, R4 and Cv values, or the equivalents thereof in different capacitive sensing circuits, including analog circuits.

It should be appreciated that the indicator lights, such as either of 119a or 119b are just one on many possible means for communicating when the capacitive sensing circuit has detected a predetermined quantity of urine absorbed in a diaper material. Alternative means for communicating are vibration, noise and the transmittal of the signal to a graphic display panel on the device, as well as transmittal to any form of remote display device, SMS text message, e-mail, as well as a transmittal to a data logger, server, management information system (MIS) and the like, including any combination thereof, with such communication being wired or wireless.

In a more preferred embodiment of the invention, such as an at least partially analog circuit, may include a Bluetooth™ or other wireless transmitter that sends a measured parameter or signal, such as an output voltage or frequency shift, or any parameter representing detected urine level to an external computing device, such as a smart phone. The at least partially analog circuit further contemplates a digital burst mode charge transfer sensor, but with multi or continuous level of output of detection that can be associated with any combination of fluid amount and/or detection distance limitation. The smart phone, or other remote processor can then deploy a software program that allows the user to set the moisture detection threshold at a value they feel suitable for providing an indication of wetness that is useful, and more preferably at a distance appropriate to the clothing being worn over the diaper. In other words, the software program allows the setting of an alert threshold at a level of the diaper urine absorption they feel is suitable to indicate the diaper should be replaced or manually checked to determine if it needs to be replaced.

The smart phone under the control of such application, in addition to setting a desired threshold, such as via a GUI, can also provide a selectable timing level to remind the user to re-test or manually check the diaper at periodic intervals. The user can set the interval, or the interval can be made more frequent in proportion to the moisture level detected as well as prior use history logged by the smart phone memory or stored remotely.

One particular problem, which has been solved by shaping the electrode 150, is the user tendency to vary the orientation of the device as the distal or sensing end 111 is placed proximal to the diaper area. Shaping a sufficiently large electrode 150 to cover 2 non parallel planes 151 and 152 eliminates this variability. FIG. 3 and FIG. 8A-D illustrate such an electrode 150. FIG. 9B illustrates another variant of such an electrode 150. Planar and connected portions 152 and 151 of electrode 150 are non-parallel, being disposed at right angle, and connected by another non-parallel planar portion 153. The electrode 150 can be curvilinear or have planar and curvilinear portions. The electrode 150 is optionally shaped to have adjacent portions that match the non-planar shape at the distal end of the housing.

Figure 9A:
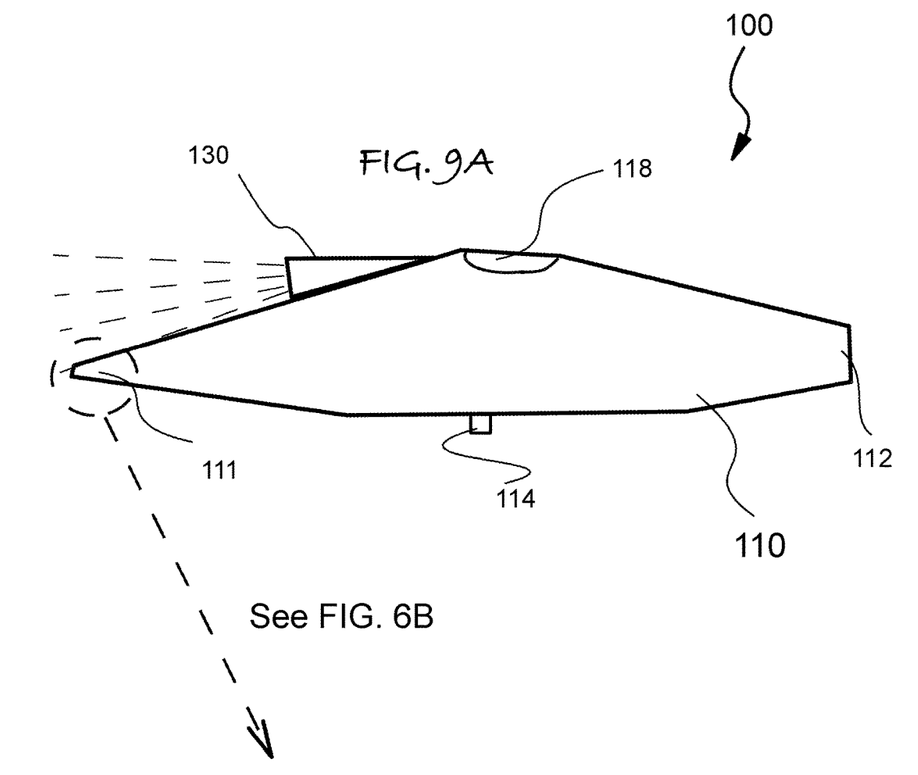
Figure 9B:
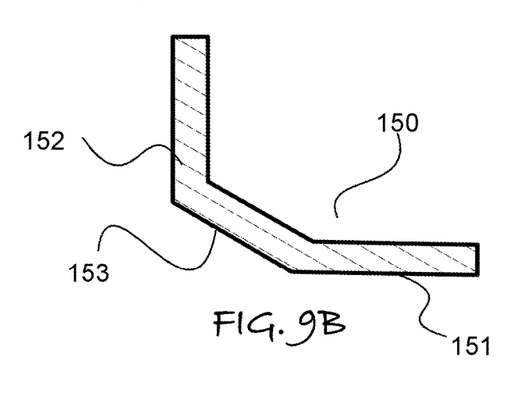
FIG. 9B is an enlarged sectional elevation view of an alternative embodiment of the electrode for any of the circuits.
Figures 10A, 10B:
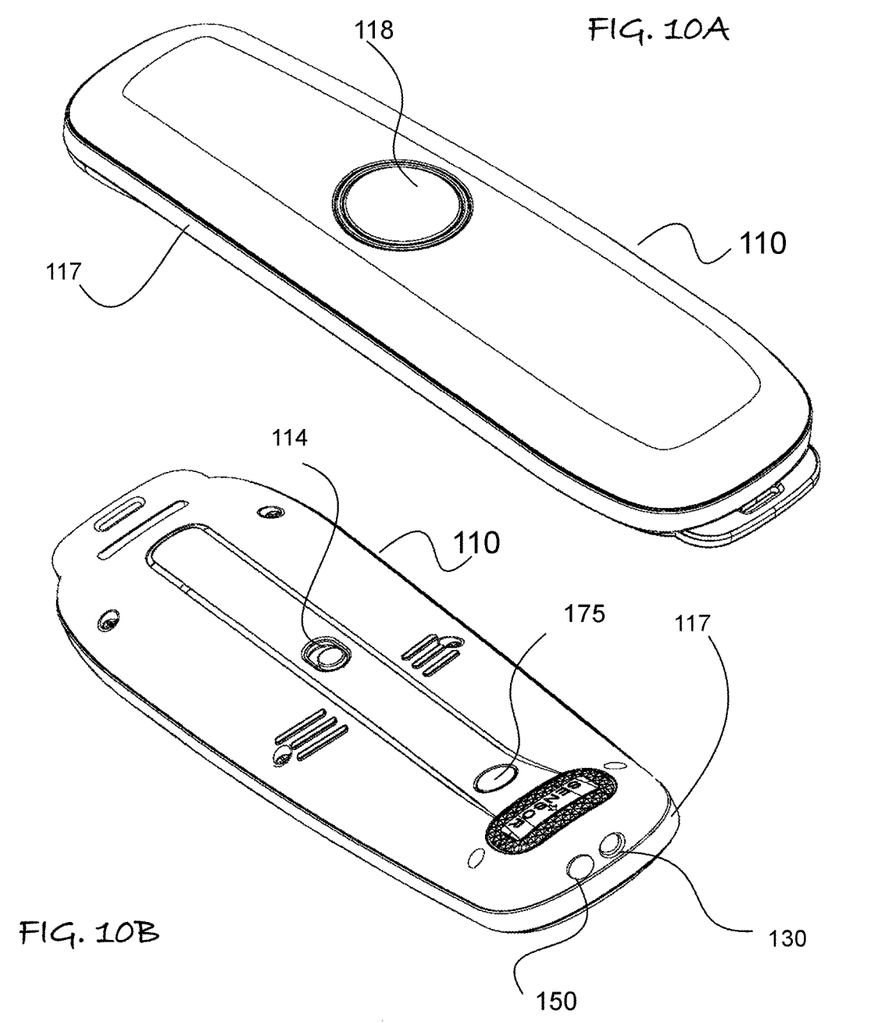
FIGS. 10A and 10B are respectively top and bottom perspective views of another alternative embodiment of the sensor.
Figures 11A, 11B, 11C, 11D, 11E:
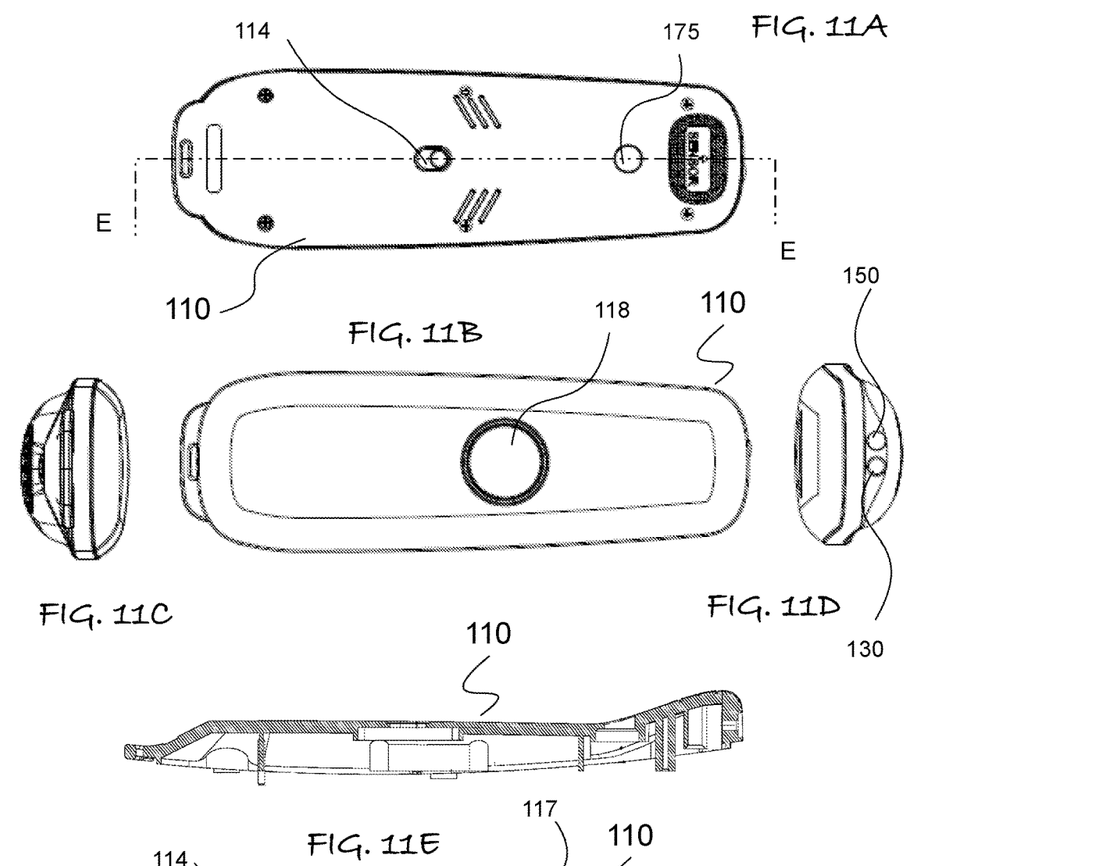
FIG. 11A-F are respectively the bottom plan view, top plan view, rear elevation view, front elevation view, cross-sectional elevation view (at section line E-E in FIG. 11B) and side elevation view of the embodiment of FIGS. 10A and 10B.
Figure 11F:
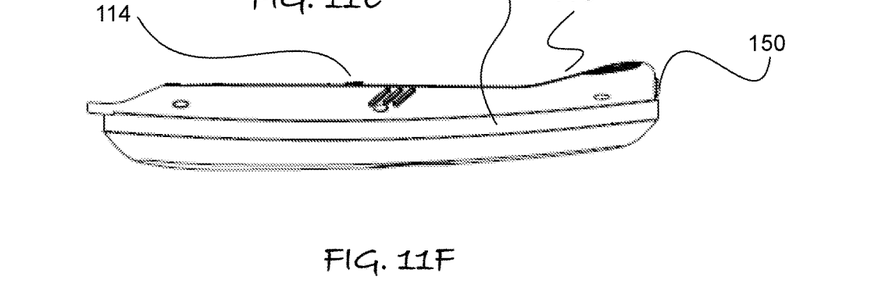
Figure 12:
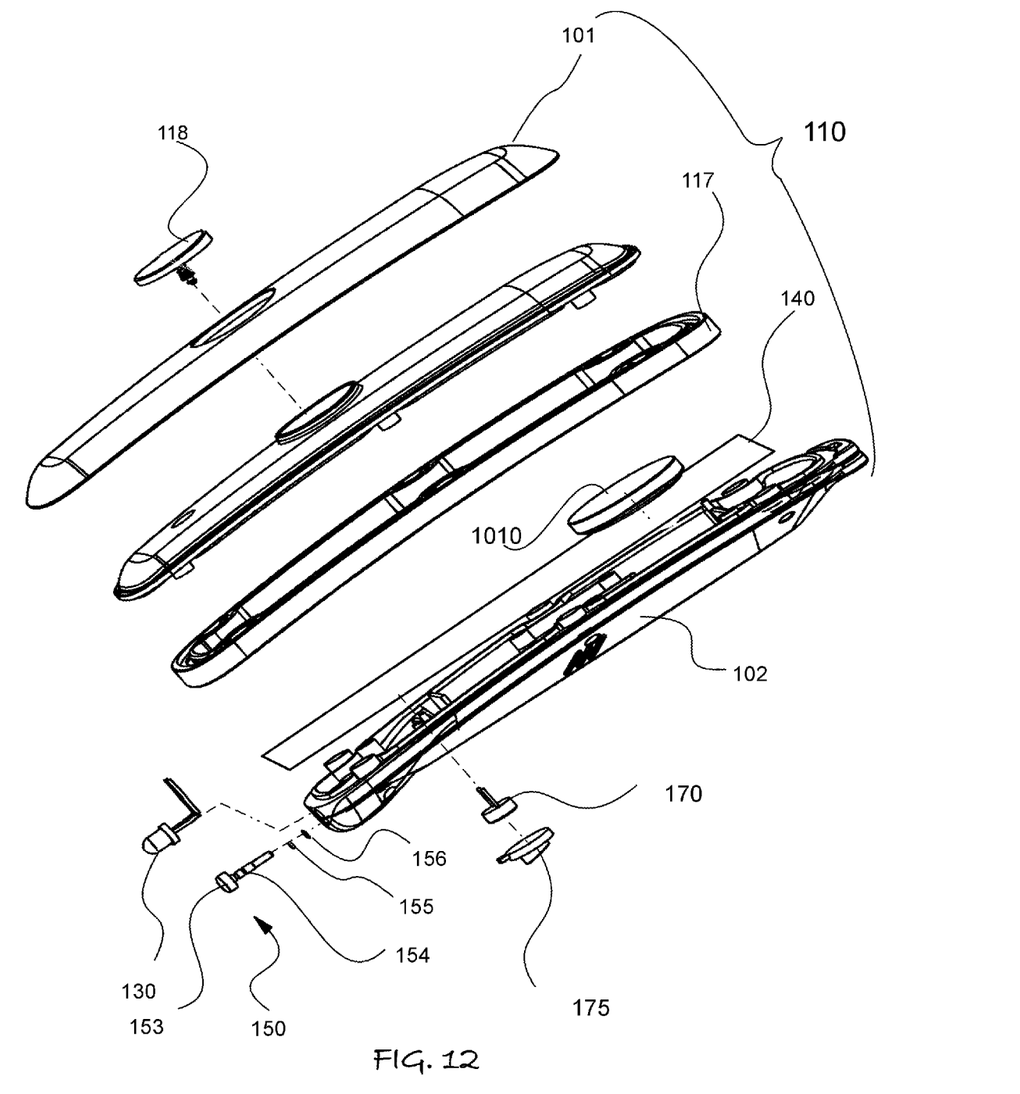
FIG. 12 is an exploded perspective view of the embodiment of FIG. 10A-11F.

Since the urine detecting sensor is expected to be used by caretakers around the clock, in the more preferred embodiment of FIG. 9A, it also has an integrated external light 130 in the housing 110 so the user can illuminate the subject wearing the diaper and bring the active electrode 150 part of the capacitive circuit contained therein in proximity to the subject. The light 130 in the housing 100 is also configured to illuminate the tip 111 of the sensor devise 100 so the user can visualize the sensor tip and diaper from the same handheld light.

In a more preferred mode, the light 130 or an additional light, can have a focal point set at the proper sensing distance. Hence, the user can bring the light progressively closer to the user until the focal point image becomes the clearest.

The connector coupling 125, can optionally have either of mating portion 125a and 125b molded into the distal end 112 of the sensor body 100, as well as attached with cord 121. In the preferred embodiment coupling portion 125b is double injection molded to be incorporated in to the portion of the strap 123b that opposes the loop 122.

Alternatively, light indicators 119a and 119b are optionally multi color LED's. In the preferred mode of using the sensor 100 as a diaper urine detector, one color represents an essentially dry or fresh diaper. Another light or external lighting state can indicate can indicate that some urine is absorbed by the diaper, but below the threshold of the holding capacity which would require changing the diaper. Another color can represents the capacitive circuit detecting moisture sufficiently close to the diaper capacity that the diaper should be promptly changed. The intermediate state color indicates to the user that they should take more frequent measurements so that they promptly detect the moisture absorption that would be indicated by other light colors, and require the diaper to be changed promptly to prevent diaper rash. Alternative indicators include multiple lights that show the gradual stages of moisture detection in finer increments, such as 3-5 stages before the final indicator showing the necessity to change the diaper. Alternatively, detected moisture levels can be provided to the caretaker/user as an alphanumeric readout on a digital display on the device housing 110.

Another benefits of the sensor 100 and housing 110 disclosed herein are that the sensor 110 is conveniently attached to the outside of a travel bag or a fixed object at a work space by the strap 120. The strap 120 avoids misplacement, loss and/or damage from being dropped. The strap 120 also provides the sensor 100 in convenient reach at the point of use. In the more preferred embodiments, the strap 120 is sufficiently long to allow use while still attached to a portable or fixed object by the strap 120.

FIG. 10-13 depicts a more preferred embodiment of the invention that includes aspects and elements particularly suitable for the testing and management of incontinence for adults that wear absorbent pads, i.e. adults diapers. The detection of moisture in adult diapers posses different problem because the diapers are larger and hold a larger quantity of fluid. Depending on the size of the diaper, as fit to the user, it is desirable to change the diaper when the fluid has reached about 150 cc for smaller adult diapers, and between about 180 to 200 cc for larger adult diapers. In addition, with the larger adult diapers it is desirable that the detect sensitivity is not greatly influenced by the residence time in the diaper, as a small amount of fluid will dually diffuse throughout the diaper. It is desirable to detect and change the diaper before the full capacity is reached, so as to avoid leakage between diaper checks. However, it is also undesirable to change the diapers too prematurely due to the time it takes for caregivers, and annoyance of the wearer. Hence, it is desired that the device is not triggered by concentrated urine that will eventually diffuse, and it is desirably to sense a large quantity of urine that has already spread within the absorbent material within the diaper.

It has been discovered that the desired sensitivity can be achieved with a different electrode shape and placement than the infant/child diaper sizes discussed with respect to FIG. 4A through 9B.

For sensing about 150 to 200 ml of fluid, the electrode 150 has a rivet or nail type shape with the metal head or tip 153 outside of the housing 111, and the shaft 154 extending inside the housing 110 to connect with the PCB 114. The tip-housing interface is sealed with one or more round gasket 155 and 156.

Figure 13A:
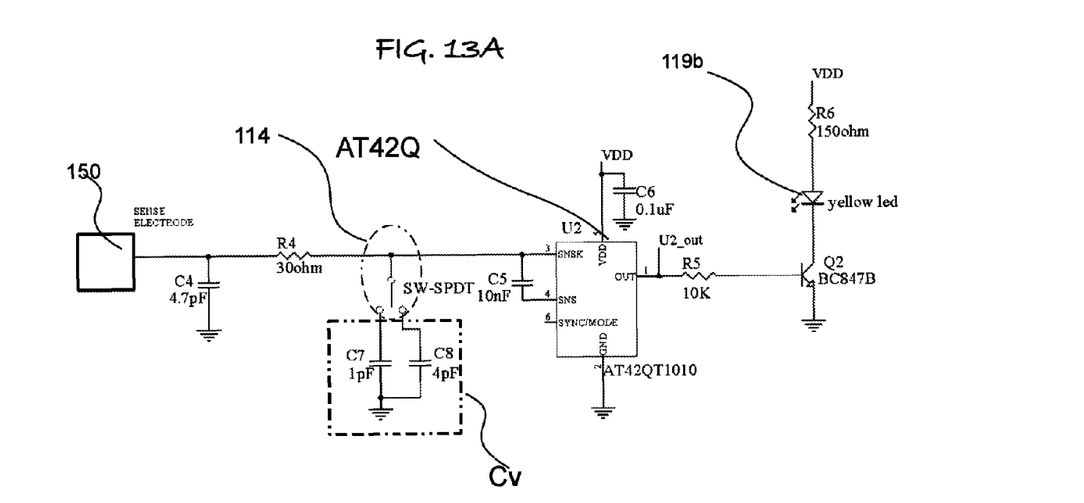
FIGS. 13A and 13B are schematic circuit diagram of a portion of the portion of the sensing circuit that corresponds to FIG. 6A, that are adapted to work with the electrode configuration and desired fluid sensing volume for the embodiments of FIG. 10A-12.
Figure 13B:
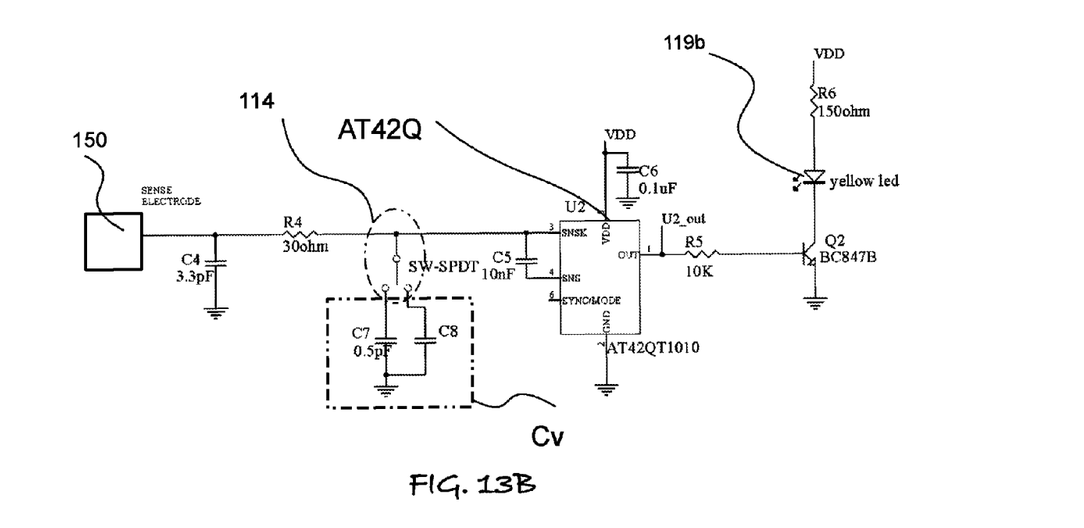

The round or circular shape of the head or tip 153 minimizes detection signal various with orientation with the version of the circuit shown in FIG. 13A-B.

The sensor and housing 100 includes the integrated external light 130 in the housing 110 so the user can illuminate the subject wearing the diaper and bring the active electrode 150 part of the capacitive circuit contained therein in proximity to the subject. However, in this embodiment, the light 130 is laterally adjacent to the electrode head 153 at the tip 111 of the sensor devise 100.

The circuit of FIGS. 13A and 13B are configured to enable a greater detection volume by adjusting the values of Cv between different alternative combination, such as in FIG. 13A in which Cv is selected as either 1 pF (C7) or 4 pF (C8) via the switch 114.

Alternatively as shown in FIG. 13B, Cv can be as low as 0.5 pF (C7) and any higher value of C8, which is preferably from about 2 to 8 pF.

The components R4, C4, C7 and C8 can also be selected by switch 114 to vary the sensitivity to account for difference in clothing thickness worn by a patient, as well as the volume of fluid in the diaper. In the case of an analog output to the capacitive circuit, such as the preferred digital burst mode charge transfer mode sensor, the continuous output level can be analyzed by an IC or microprocessor either on the PCB 140 or externally in signal communication to account for one of more of diaper size, urinary volume and frequency of the patient, clothing worn, and past measurements in the same diaper to infer that the diaper should be changed promptly, or another measurement should be taken within a given amount of time. Additionally, the sensor device may have fixed R4, C4 and Cv values and still provide useful advice to care givers when the sensitivity accounts for a typical range of clothing thickness and absorbed urine in the diaper.

The housing 110 also contains a means to preserve battery life such that the flashlight only is able to be energized when a detector, such as the photoresistor/photodiode 170 in signal communication with the circuit 1010 to only energize the light 130, when the device 100 is in a room with insufficient light, and optionally only when the switch 118 is activated to energize the circuit 1010. Preferably the photoresistor is covered by a lens 175 at the exterior or the housing that collects external light and directs it to the photoactive surface of the photoresistor device 170.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

We claim:

1. A device for sensing comprising:
   a) a portable housing, b) a capacitive sensing circuit disposed in the housing and having;
  i) a sensing electrode disposed at a distal end of the housing,
  ii) an source of illumination of the field of use of the sensing device that is at least one of directed towards or emanating from the distal ends of the housing,
  iii) a source of power for energizing the circuit,
  iv) at least one externally visible indicator light that is energized by the power source when the capacitive circuit has detected a quantity of urine from a distance without the sensing electrode making contact with the urine.

2. The device for sensing according to claim 1 wherein the capacitive sensing circuit has an external switch to adjust the sensitivity of the device.

3. The device for sensing according to claim 1 wherein the capacitive sensing circuit is a digital burst mode charge transfer sensor.

4. The device for sensing according to claim 3 wherein the capacitive sensing circuit has an external switch to adjust the sensitivity of the device.

5. The device for sensing according to claim 4 wherein the external switch is operative to select from 2 or more capacitors that are operative to adjust the sensitivity of the device.

6. The device for sensing according to claim 1 wherein the capacitive sensing circuit deploys an electrode with connected planar portions that are not in parallel planes to each other.

7. The device for sensing according to claim 1 wherein the capacitive sensing circuit deploys an electrode with a pin shape terminating in a head that is disposed outside the elongated housing.

8. The device for sensing according to claim 1 wherein the capacitive sensing circuit is a digital burst mode charge transfer sensor with;
  a) a resistive component in series connection to the sensing electrode,
  b) a first capacitor component connecting said resistive component to the digital burst mode charge transfer sensor,
  c) a second capacitive component connected to ground in a parallel circuit between said resistive component and said first capacitor.

9. A device for sensing comprising:
c) a portable housing,
d) a capacitive sensing circuit disposed in the housing and having;
  i) a sensing electrode disposed at a distal end of the housing,
  ii) a source of power for energizing the circuit,
  iii) a means for communicating when the capacitive sensing circuit has detected a predetermined quantity of urine absorbed in a diaper material wherein the capacitive sensing circuit has an external switch to adjust the sensitivity of the device.

10. The device for sensing according to claim 9 wherein the capacitive sensing circuit is a digital burst mode charge transfer sensor.

11. The device for sensing according to claim 9 wherein an external switch is operative to select from 2 or more capacitors.

12. The device for sensing according to claim 9 wherein the capacitive sensing circuit deploys an electrode with connected planar portions that are not in parallel planes to each other.

13. The device for sensing according to claim 7 wherein the source of illumination of the field of use of the sensing device is disposed at the distal ends of the housing adjacent the head that is disposed outside the elongated housing.

14. The device for sensing according to claim 13 wherein the capacitive sensing circuit is a digital burst mode charge transfer sensor with;
  a) a resistive component in series connection to the sensing electrode,
  b) at least one first capacitor component for connecting said resistive component to the digital burst mode charge transfer sensor,
  c) a second capacitive component connected to ground in a parallel circuit between said resistive component and said first capacitor.

15. The device for sensing according to claim 14 and further comprising an external switch that is operative to select from two or more of the at least one first capacitive component to adjust the sensitivity of the device.

16. The device for sensing according to claim 9 wherein the capacitive sensing circuit is a digital burst mode charge transfer sensor with;
  a) a resistive component in series connection to the sensing electrode,
  b) at least one first capacitor component for connecting said resistive component to the digital burst mode charge transfer sensor,
  c) a second capacitive component connected to ground in a parallel circuit between said resistive component and said first capacitor.

* * * * *